United States Patent [19]

Buysch et al.

[11] Patent Number: 5,498,742
[45] Date of Patent: Mar. 12, 1996

[54] PROCESS FOR THE CONTINUOUS PREPARATION OF DIARYL CARBONATES

[75] Inventors: Hans-Josef Buysch; Carsten Hesse; Johann Rechner, all of Krefeld; Reinhard Schomäcker, Leverkusen; Paul Wagner, Düsseldorf; Dieter Kaufmann, Goslar, all of Germany

[73] Assignee: Bayer Aktiengesellschaft, Leverkusen, Germany

[21] Appl. No.: 379,384

[22] Filed: Jan. 27, 1995

[30] Foreign Application Priority Data

Feb. 2, 1994 [DE] Germany ............... 44 03 075.4

[51] Int. Cl.$^6$ ............................................. C07C 68/00
[52] U.S. Cl. ............................................. 558/274; 558/271
[58] Field of Search ........................... 558/274, 271

[56] References Cited

U.S. PATENT DOCUMENTS 4,201,721  5/1980  Hallgren .

FOREIGN PATENT DOCUMENTS 0350700  1/1990  European Pat. Off. .
0450442  10/1991  European Pat. Off. .
2738437  4/1978  Germany .

OTHER PUBLICATIONS

Derwent Chemical Abstract, Abstract No. JP04257546–A, Week 9243 (1992).
Derwent Chemical Abstract, Abstract No. JP04261142–A, Week 9244 (1992).

Primary Examiner—Johann Richter
Assistant Examiner—Michael G. Ambrose
Attorney, Agent, or Firm—Sprung Horn Kramer & Woods

[57] ABSTRACT

The invention relates to a process for the continuous preparation of diaryl carbonates by reaction of an aromatic hydroxyl compound with carbon monoxide and oxygen in the presence of a catalyst containing a noble metal of group VIIIb of the Periodic Table of the Elements, a quaternary salt, a cocatalyst and a base. The catalyst is activated by treatment with carbon monoxide in the liquid phase. The reaction water is removed by excess reaction gas.

20 Claims, 3 Drawing Sheets

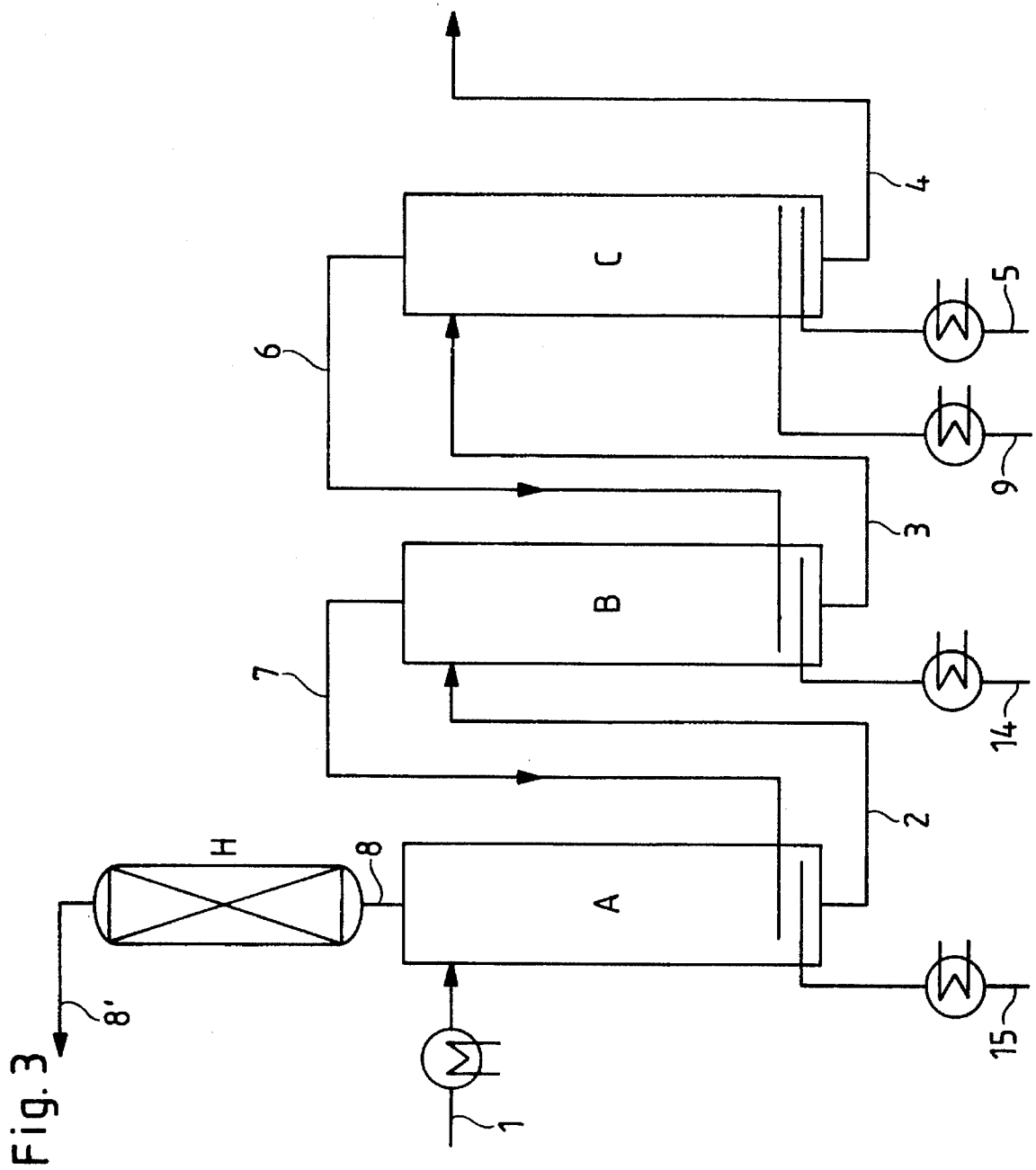

PROCESS FOR THE CONTINUOUS PREPARATION OF DIARYL CARBONATES

BACKGROUND OF THE INVENTION

1. Field of the Invention

The present invention relates to a process for the preparation of diaryl carbonates by reaction of an aromatic hydroxyl compound (e.g. phenol) with carbon monoxide and oxygen in the presence of a catalyst, a cocatalyst, a quaternary salt and a base which is characterized in that water is continuously removed with the reaction gas by stripping.

2. Description of the Related Art

It is known to prepare organic carbonates by oxidative reaction of an aromatic hydroxyl compound with carbon monoxide in the presence of a noble metal catalyst and a cocatalyst (German Offenlegungsschrift 2 738 437). The noble metals proposed are the elements of group VIIIb, palladium being preferably used. During the reaction, this palladium(II) species is reduced to palladium(0) and oxidized back to palladium(II) by oxygen with the aid of a cocatalyst. The cocatalysts used can be various manganese salts or cobalt salts in different oxidation states. In addition to these cocatalysts, a base, a quaternary ammonium salt and a desiccant are used. The solvent used is preferably methylene chloride.

In addition to the use as solvent of methylene chloride which is highly volatile, can be converted in the event of fire into phosgene, requires high expense for safety measures and must be recovered in a cost-intensive manner, disadvantages of this process are long reaction times and the poor space-time yields associated therewith. However, for an industrial reaction, the unsatisfactory reproducibility proves to be a decisive disadvantage, since from batch to batch, with an identical procedure, highly variable results can be obtained, even complete failure of catalysis.

In EP 350 700, the use of various cobalt salts, preferably cobalt acetate, is proposed as cocatalyst. In addition to this cocatalyst, the use of considerable amounts of various quinones or hydroquinones as an electron transfer catalyst is proposed. Separating off the electron transfer catalyst from the reaction mixture requires considerable expenditure in this process. Moreover, hydroquinones represent an additional aromatic bifunctional hydroxyl compound which can be reacted in the same manner to give carbonates. Separating off the byproducts formed in this manner can only be achieved with great expense. Recovery of the electron transfer catalyst used is not possible. The formation of these byproducts considerably decreases the selectivity and thus the economic efficiency of this process. The problem of inadequate reproducibility is also not solved in this application.

In the process proposals mentioned, the addition of a molecular sieve to bind water is necessary. In the absence of a molecular sieve, the conversion rate achievable turns out markedly lower, since carbonate formed is hydrolysed by reaction water formed at the same time. However, the use of molecular sieves makes the process unattractive for industrial use, since, for an effective separation of the water from the liquid phase, large amounts of molecular sieve (100 to 500% excess) are required which must be regenerated at high expense. The use of carbon dioxide as desiccant is proposed in EP 450 442. For this purpose approximately 30 to 35% of carbon dioxide is added to the reaction gas which is composed of oxygen and carbon monoxide. Considerable amounts of quinones/hydroquinones are also added here as electron transfer catalyst. The problems occurring owing to the addition of electron transfer catalysts with respect to byproduct formation, poor selectivity and loss of catalyst are, as already described above, also serious disadvantages here. Furthermore, the use of carbon dioxide as desiccant does not constitute an advantage. This is made clear by two essential points:

Firstly, carbon dioxide is only poorly suitable for drying the reaction mixture. This follows clearly from comparison of the examples in EP 450 442 (desiccant carbon dioxide) and EP 350 700 (desiccant molecular sieve). Thus in the presence of the desiccant carbon dioxide after 5 hours of reaction time only about one third of the yield is achieved which is obtained in the same time with molecular sieve as desiccant. Because of its low efficacy, carbon dioxide must be added in large amounts (approximately 35% of the reaction gas). This leads to a great dilution of the reaction gas, as a result of which the space-time yields achievable are dramatically decreased. Finally, in the event of circulation of the reaction gas, as the industrial conversion of this process requires, accumulation of the carbon dioxide in the gas stream must be prevented by complex processes. This additionally requires a high expenditure in terms of apparatus and high costs associated therewith which make economical utilization of this process impossible just for this reason.

Secondly, carbon dioxide does not behave in an inert manner to the reaction components. Bases such as, for example, sodium hydroxide can react with carbon dioxide to form insoluble products. As a result the catalyst system can be deactivated to the extent that no carbonate formation occurs any longer. Simultaneous use of carbon dioxide as desiccant and base in the catalyst system is therefore impossible.

In JP 04/257 546, a process is described in which the reaction with carbon monoxide in the presence of a noble metal catalyst and a quaternary salt is carried out by continuous feed into a distillation column. The reaction water is continuously distilled off.

It is a disadvantage in this process that, in order to remove the reaction water, the procedure must be performed in a distillation column which, owing to its construction, makes possible only short residence times. The space-time yields achievable by this process are therefore, at only 17.8 g/lh, very low.

This process disadvantage is particularly serious against the background of the extremely high catalyst usage which is necessary for these space-time yields. Thus in Example 1 of the application, at a loading of 182 g of phenol per hour, in total 3 g/h of palladium compound and 14.4 g/h of quaternary ammonium salt are used. At a reported yield of 35 g of diphenyl carbonate per hour, in one hour only 16.3 catalyst cycles are therefore achieved. This means that to prepare one kilogram of diphenyl carbonate by this process, at least 30 g of pure palladium (corresponding to 90 g of palladium compound) are needed. This requires very high capital costs for the catalyst and, additionally, high expense for the recovery of the noble metal. Economic utilization of the process is thus impossible. The use of large amounts of halides at high temperatures of 150° to 180° C., as required in this process, leads to great corrosion problems which involve high expenditure in terms of apparatus. It is further known to those skilled in the art that under the reaction conditions quoted the iodide of the quaternary salt preferably used is not stable and is oxidized to iodine to a considerable extent. This leads to great losses of the quaternary salt and to the formation of byproducts which greatly impairs the selectivity and thus the economic efficiency of this process.

In JP 04/261 142, a process is described in which the procedure is followed as in JP 04/257 546, with the difference that additional reactors are mounted on the distillation column to increase the residence time. The abovementioned problems with corrosion, catalyst consumption and loss of quaternary salt and the side reactions associated therewith are also not solved in this application. The proposed equipment likewise brings no advantages. The residence time is increased by the additional reactors. However, the proposed construction leads to a considerable back-mixing within the equipment so that side reactions can proceed to an increased extent, as a result of which the selectivity decreases. Thus in illustrative Example 1 of JP 04/261 142, a selectivity of only 97% is achieved in comparison with 99% in the comparable Example 1 of JP 04/257 546. The space-time yields achievable by this process are at approximately 9 g/l h lower still than with JP 04/257 546. Effective removal of the reaction water is impossible owing to the additionally mounted reactors. For in the proposed procedure, the reaction water formed in the reactors during the reaction is only removed subsequently in the distillation column. Under the reaction conditions, the carbonate formed in the reactors is cleaved again hydrolytically, as a result of which only very low conversion rates are achievable. In no application mentioned is the problem of unsatisfactory reproducibility solved so that, overall, a process which can be converted to an industrial scale has not hitherto been available.

The object was therefore to find a process which permits performing the synthesis of aromatic carbonates with continuous removal of the resulting reaction water at a high space-time yield under economic, industrially realizable and reproducible conditions.

SUMMARY OF THE INVENTION

Surprisingly it has now been found that the continuous preparation of diaryl carbonates can be performed by oxidative reaction of an aromatic hydroxyl compound in the presence of a noble metal catalyst, a cocatalyst, a quaternary salt and an alkali metal phenolate as base at a high space-time yield and very low catalyst consumption, if the resulting reaction water is continuously stripped off from the reaction solution with excess reaction gas.

The invention consequently relates to a process for the preparation of an organic carbonate of the formula (I)

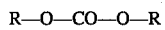  (I)

in which

R denotes an unsubstituted or substituted $C_6$–$C_{12}$-aryl, preferably an unsubstituted or substituted $C_6$-aryl, particularly preferably phenyl, by reacting an aromatic hydroxyl compound of the formula (II),

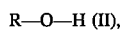, in which

R has the meaning given above,
with carbon monoxide and oxygen in the presence of a noble metal catalyst which was prepared from a compound of a noble metal of group VIIIb of the Periodic Table of the Elements (Mendeleev) in the presence of a quaternary salt by treatment with carbon monoxide in liquid phase at elevated temperature, a cocatalyst, a quaternary salt and a base, which is characterized in that the reaction water is removed from the reaction mixture by excess reaction gas.

BRIEF DESCRIPTION OF THE DRAWINGS

The accompanying drawings (FIG. 1, 2, and 3) show, by way of example, arrangements of reactors (an individual reactor or a cascade of three reactors) to continuously carry out the inventive process.

DETAILED DESCRIPTION OF THE INVENTION

Figure 1:
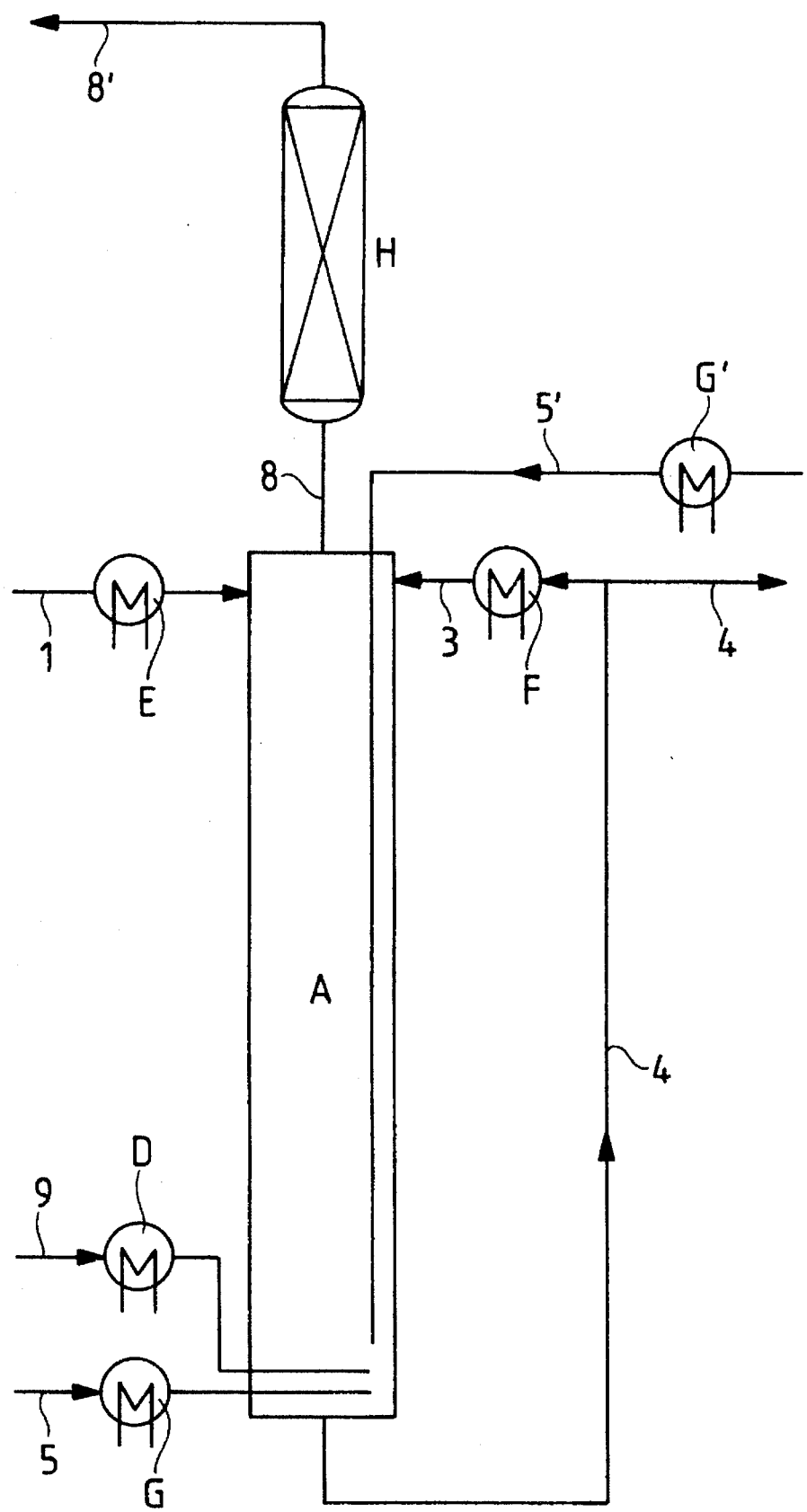

The reaction gas, composed of carbon monoxide, oxygen and an inert gas, is introduced for this purpose at a rate of 1 to 100,000 l (S.T.P.) per liter of reaction solution, preferably 5 to 50,000 l (S.T.P.) per liter of reaction solution and particularly preferably 10 to 10,000 l (S.T.P.) per liter of reaction solution.

The composition of the reaction gases carbon monoxide and oxygen can be varied in broad concentration ranges. However, expediently a $CO:O_2$ molar ratio (normalized on CO) of 1:(0.001–1.0) is established, preferably 1:(0.01–0.5) and particularly preferably 1:(0.02–0.3). The oxygen partial pressure at these molar ratios is high enough in order to be able to achieve high space-time yields and at the same time not to be able to form explosive carbon monoxide/oxygen gas mixtures. The reaction gases are not subject to special purity requirements, so synthesis gas can serve as CO source and air as $O_2$ carrier, but care must be taken to ensure that no catalyst poisons such as sulphur or compounds thereof are introduced. In the preferred embodiment of the process according to the invention, pure CO and pure oxygen are used. In a further preferred embodiment of the process according to the invention, CO and oxygen are added independently of each other. The oxygen addition, in this case, can take place, if desired, together with inert gas. When a reactor cascade is used instead of an individual reactor, the separate oxygen addition preferably proceeds in such a way that the optimal oxygen concentration is ensured in each of the reactors.

Inert constituents of the reaction gases in the process according to the invention can be nitrogen, hydrogen, noble gases and organic compounds stable under reaction conditions which form an azeotrope with water. The concentration of inert gas in the reaction gas can be 0–30% by volume, preferably 0–15% by volume, particularly preferably 0–5% by volume. The concentration 0% by volume represents the special case of the preferred inert gas-free state.

By means of a separation element situated in the exhaust gas stream such as a dephlegmator, distillation columns having trays or packing and other apparatuses known to those skilled in the art, the majority of the entrained phenol and/or solvent can be returned again to the reactor. The water-enriched excess reaction gas is, in the preferred embodiment, returned again to the reactor after separating off water. Water is separated off from the reaction gas in accordance with the prior art, e.g. by adsorption, absorption or preferably by cooling the pressurized gas and condensation of the water (Ullmann's Encyclopedia of Industrial Chemistry, 5th Edition, Volume A5, pages 203 et seq., Weinheim 1986; Ullmann's Encyclopedia of Industrial Chemistry, 5th Edition, Volume A12 (1989), pages 169 et seq.).

The aromatic hydroxyl compounds to be used in the process according to the invention are, for example, phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol and 2-naphthol, preferably phenol. In the case of substitution of the aromatic hydroxyl compound, this is generally 1 or 2 substituents having the meaning $C_1$–$C_4$-alkyl, $C_1$–$C_4$-alkoxy, fluorine, chlorine or bromine.

For the process according to the invention, as desired, either organic or inorganic bases or mixtures thereof can be used. Examples of inorganic bases which may be mentioned, without restricting the process according to the invention, are alkali metal hydroxides and alkali metal carbonates, alkali metal carboxylates or other salts of weak acids or alkali metal salts or aromatic hydroxyl compounds of the formula (II), e.g. alkali metal phenolates. Obviously, the hydrates of alkali metal phenolates can also be used in the process according to the invention. An example of such a hydrate which may be mentioned is sodium phenolate trihydrate. However, the amount of water added must preferably be measured in such a way that, per mol base, at most 5 mol of water are added. Higher water concentrations lead, inter alia, to poorer conversion rates and decomposition of carbonates formed. Organic bases which may be mentioned, without restricting the process according to the invention, are tertiary amines which bear as organic radicals $C_6$–$C_{10}$-aryl, $C_7$–$C_{12}$-aralkyl and/or $C_1$–$C_{20}$-alkyl or represent pyridine bases or hydrogenated pyridine bases, for example triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxyl compound, particularly preferably an alkali metal salt of the aromatic hydroxyl compound which is also to be converted to the organic carbonate. These alkali metal salts can be lithium salts, sodium salts, potassium salts, rubidium salts or caesium salts. Lithium phenolate, sodium phenolate and potassium phenolate are preferably used, particularly preferably sodium phenolate.

The base can be added to the reaction mixture as a pure compound in solid form or as a melt. In a further embodiment of the invention, the base is added to the reaction mixture as a solution which contains 0.1 to 80% by weight, preferably 0.5 to 65% by weight, particularly preferably 1 to 50% by weight of the base. The solvents which can be used here are both alcohols or phenols, such as the phenol to be reacted, and inert solvents. Examples of solvents which may be mentioned are dimethylacetamide, N-methylpyrrolidinone, dioxane, t-butanol, cumyl alcohol, isoamyl alcohol, tetramethylurea, diethylene glycol, halogenated hydrocarbons (e.g. chlorobenzene or dichlorobenzene) and ethers. These solvents can be used alone or in any combination with each other. Thus one embodiment of the process according to the invention comprises, for example, dissolving the base in a phenol melt which was diluted with a solvent. The base is preferably dissolved in the melt of an aromatic hydroxyl compound, particularly preferably in a melt of the aromatic hydroxyl compound which is to be reacted to give the organic carbonate. The base is very particularly preferably added dissolved in phenol.

The base is added in an amount independent of the stoichiometry. The ratio of palladium to base is preferably chosen in such a way that, per mol of palladium, 0.1 to 500, preferably 0.5 to 200, particularly preferably 0.9 to 130 equivalents of base are used.

The process according to the invention is preferably carried out without solvent. Obviously, inert solvents can also be used. Those which may be mentioned are those mentioned above in connection with the base.

The noble metal catalysts suitable for the process according to the invention are composed of at least one metal of group VIII, preferably palladium. The noble metal can be added for example in the process according to the invention in various forms. Palladium can be used in metallic form or, preferably, in the form of palladium compounds of oxidation states 0 and +2, such as palladium(II) acetylacetonate, palladium(II) halide, palladium (II) carboxylate of $C_2$–$C_6$-carboxylic acids, palladium(II) nitrate, palladium(II) oxide or palladium complexes which can contain, for example, olefines, amines, phosphines and halides. Palladium bromide and palladium acetylacetonate are particularly preferred.

The amount of noble metal catalyst is not restricted in the process according to the invention. Enough catalyst is preferably used so that its concentration, calculated as metal, is 10 to 3,000 ppm in the reaction batch, concentrations of 10 to 1,000 ppm are preferred, 50 to 1,000 ppm are particularly preferred. The catalysis cycles achievable, i.e. the number of moles of diarylcarbonate formed per mol of palladium and hour are 1 to 50,000, preferably 100 to 30,000.

The cocatalyst used for the process according to the invention is a metal compound of groups III A, IV A, V A, I B, II B, VI B or VII B of the Periodic Table of the Elements (Mendeleev), where the metal can be used in various oxidation states. Without restricting the process according to the invention, manganese (II), manganese(III), copper(I), copper(II), cobalt(II), cobalt(III), vanadium(III) and vanadium(IV) may be mentioned. The metals can be used, for example, as halides, oxides, carboxylates of $C_2$–$C_6$-carboxylic acids, diketonates or nitrates or as complex compounds which can contain, for example, carbon monoxide, olefines, amines, phosphines and halides. Manganese compounds are preferably used in the process according to the invention, particularly preferably manganese(II) complexes, very particularly preferably manganese(II) acetylacetonate.

The cocatalyst is added in an amount such that its concentration is in the range from 0.001 to 20% by weight of the reaction mixture, preferably in the concentration range from 0.005 to 5% by weight, particularly preferably 0.01 to 2% by weight.

The quaternary salts used in the context of the present invention can be, for example, salts of ammonium or phosphonium substituted by organic radicals. Ammonium salts and phosphonium salts which bear $C_6$–$C_{10}$-aryl, $C_7$–$C_{12}$-aralkyl and/or $C_1$–$C_{20}$-alkyl radicals as organic radicals and a halide, tetrafluoroborate or hexafluorophosphate as anion are suitable for use in the process according to the invention. Ammonium salts which bear $C_6$–$C_{10}$-aryl, $C_7$–$C_{12}$-aralkyl and/or $C_1$–$C_{20}$-alkyl radicals as organic radicals and a halide as anion are preferably used in the process according to the invention, particularly preferably tetrabutylammonium bromide.

The amount of such a quaternary salt is 0.1 to 50% by weight, based on the weight of the reaction mixture. This amount is preferably 0.5 to 15% by weight, particularly preferably 1 to 5% by weight.

The process according to the invention is carried out, preferably without solvent, at 30° to 200° C., preferably at 30° to 150° C., particularly preferably at 40° to 120° C. at a pressure of 1 to 100 bar, preferably 2 to 50 bar, particularly preferably at 5 to 25 bar.

The space-time yields of diaryl carbonate achievable by the process according to the invention, i.e. the amount of diaryl carbonate formed in g per liter of reactor volume and hour are 1 to 3,500 g/lh, preferably 10 to 2,500 g/lh.

The reproducibility is achieved by the procedure described below. The noble metal catalyst is activated before the reaction. For this purpose the noble metal compound is measured in such a way that the concentration of the noble metal in the activation batch is 0.0001 to 30% by weight, preferably 0.001 to 10% by weight and is dissolved in an inert solvent or directly in the melt of the aromatic hydroxyl compound or mixtures of the same. To this solution is added a quaternary salt which is one of the above-described ammonium or phosphonium salts substituted by organic radicals. This solution is then treated with carbon monoxide at 15° to 200° C., preferably at 20° to 150° C., particularly preferably at 40° to 100° C. This can be achieved both by introducing carbon monoxide at atmospheric pressure in an amount of 0.1 to 250 l/h, preferably 0.5 to 200 l/h, particularly preferably 1 to 100 l/h per gram of noble metal used, and by adding carbon monoxide to the solution in an autoclave at a pressure of 1 to 300 bar, preferably 1 to 200 bar, particularly preferably 1 to 150 bar. The activation time depends on the noble metal catalyst used and on any inert solvent used. It is generally a few minutes to a few hours, for example 0.05 to 5 h, preferably 0.1 to 3 h, particularly preferably 0.25 to 2 h. The noble metal catalyst can be activated immediately before the reaction, but also after separating off the solvent or the aromatic hydroxyl compound, e.g. by distilling, isolated and stored without loss of activity.

Reactors which are suitable for the process according to the invention are stirred tanks, autoclaves and bubble columns, these being able to be used as individual reactors or as a cascade. In a cascade, 2 to 15, preferably 2 to 10, particularly preferably 2 to 5, reactors can be connected one after the other.

To mix the reaction components to be used according to the invention, the stirred vessels are equipped with agitators useful therefor. Such agitators are known to those skilled in the art. Those which may be mentioned by way of example are: disc agitators, impeller agitators, propeller agitators, paddle agitators, multistage impulse counter-current agitators (MIG) and Intermig agitators, tubular agitators and various hollow agitator types. Preferred agitators are those which permit effective mixing of gases and liquids, for example hollow tube gas bubble agitations, propeller agitators etc. Bubble columns which can be used in the process according to the invention are the following types: simple bubble columns, bubble columns having internals, such as: bubble columns having parallel chambers, cascade bubble columns having sieve trays or perforated trays, bubble columns having packings, having static mixers, pulsed sieve-plate bubble columns, loop reactors such as: air-lift loop reactors, downflow loop reactors, jet loop reactors, free-jet reactors, jet-nozzle reactors, bubble columns having submerged liquid jets, downflow-upflow bubble columns and other bubble column reactors known to those skilled in the art (H. Gerstenberg, Chem. Ing. Techn. 61 (1979) No. 3, pp. 208–216; W. -D. Deckwer, Reaktionstechnik in Blasensäulen [Reaction Technology in Bubble Columns], Otto Salle Verlag 1985).

In the preferred embodiment, bubble column reactors and bubble column cascades are used which permit effective mixing of gas and liquids, such as cascade bubble columns and loop reactors. To maintain good mixing of liquid and reaction gas, distribution and redispersion elements can be mounted along the longitudinal axis of the bubble column reactors. Solid redispersion elements which are used are single-hole trays, perforated plates, sieve trays and other internals known to those skilled in the art.

For the first dispersion of the reaction gas in the liquid phase during addition, conventional apparatuses such as porous sinter plates, perforated plates, sieve trays, push-in tubes, nozzles, gas bubble rings and other dispersion apparatuses known to those skilled in the art.

The process according to the invention can be performed in various embodiments. One possibility is discontinuous procedure. CO and oxygen are passed into the reaction mixture either through a gas bubble stirrer, in the case of a stirred tank, or other known gas distribution elements. The reaction water is continuously removed from the reactor by the excess reaction gas. When the intended conversion rate is achieved, the reaction mixture is removed from the reactor or, if desired, worked up in the reactor.

Figure 2:
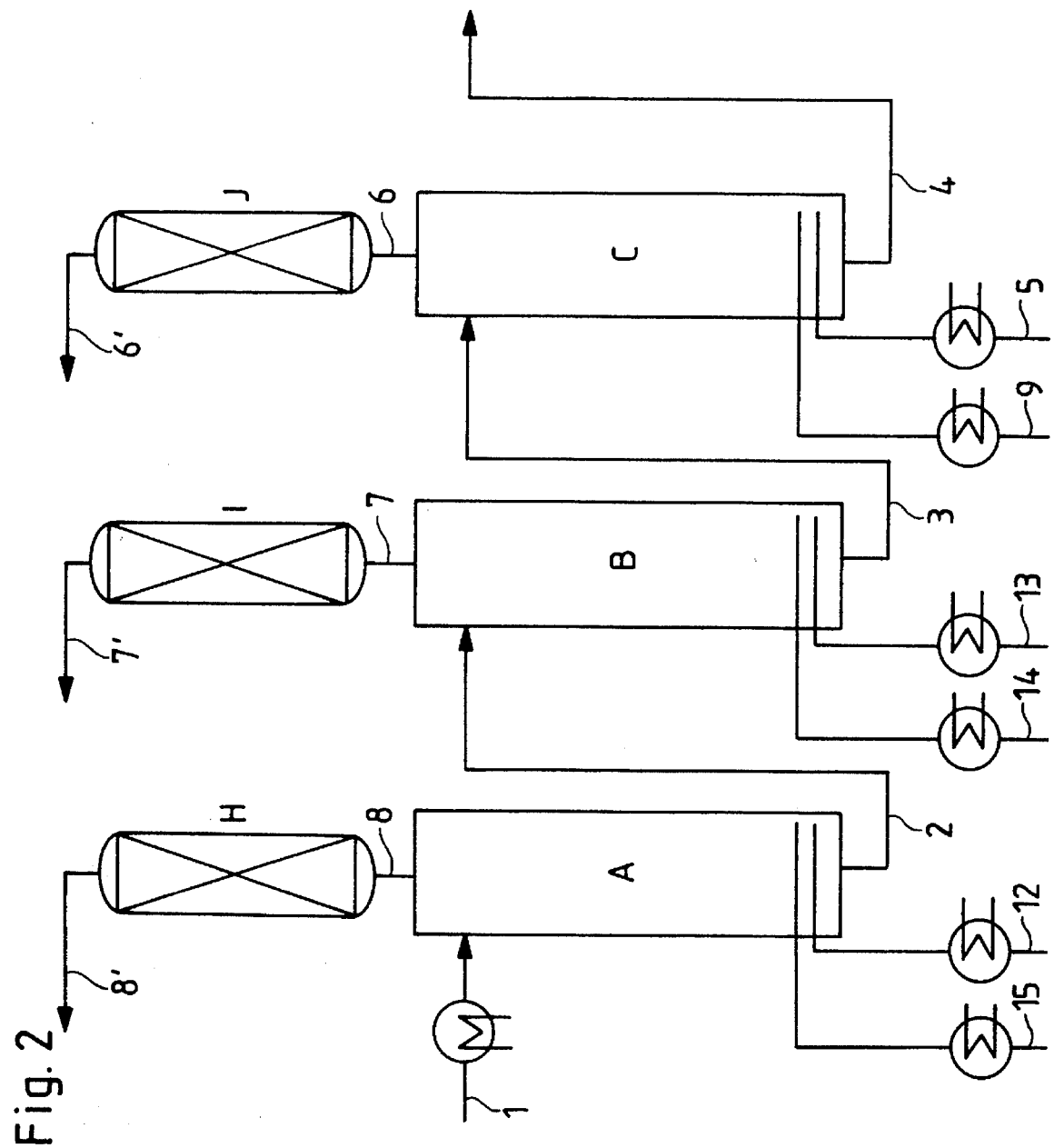

In the preferred embodiments of the process according to the invention, a continuous procedure is used in the individual reactor or in a cascade of reactors. In FIGS. 1, 2 and 3 procedures are shown by way of example using one or three reactors (A, B and C), the procedure according to the invention not being restricted to these examples.

The preferred embodiment of the process according to the invention is that the noble metal catalyst is activated in the above-described manner and this solution is then continuously added to the reactor (A) (via line (1) in FIG. 1) simultaneously with a further solution which contains the remaining components in the reaction system at the concentrations given above. By means of an upstream heater element (E), the liquid reaction components can be preheated if desired to the intended reaction temperature. The liquid phase to be removed from the reactor is taken off at the bottom reactor end and fed by the lines (4) to further processing. The desired filling level in the continuously operated reactor is controlled in accordance with the prior art. If desired, a part-stream can be returned back to the reactor (A) via line (3). By means of an upstream heater element (F), the liquid reaction components can, if desired, be preheated again to the intended reaction temperature.

The reaction gas composed of carbon monoxide, oxygen and, if appropriate, inert gas, can be introduced at the lower end of the reactor (A) via line (5) or (5') and, if desired, can be previously preheated to the reaction temperature by a preheater (G) or (G'). The oxygen can be added in this case independently of CO and inert gas or together with inert gas. In the case of separate oxygen addition, this is carried out via line (9) and preheater (D). CO and oxygen, in the amounts given above, are distributed in the reaction mixture either by a gas-introduction stirrer in the case of a stirred tank or by other known gas distribution elements. The excess reaction gas leaves the reactor together with the reaction water and entrained starting material (II) via line (8). In the separation means (H), the majority of the starting material (II) is separated off and returned to the reactor (A). The excess reaction gas leaves the reactor via line (8') together with the reaction water. The reaction water is removed from the reaction gas in accordance with the prior art. The reaction gas is then fed back to the reactor (A) together with the replacement of the reaction gas consumed.

When a reactor cascade (FIGS. 2 and 3) is used, the above-described liquid reaction components are added to the first reactor (A) and can, if desired, be preheated to the intended reaction temperature in an upstream heater element. They are introduced preferably at the upper end of the reactor in liquid form via line (1). The liquid phase to be taken off from the individual reactors is taken off at the lower reactor end and is added back at the upper end of the respective following reactors (B) or (C) via lines (2) or (3). The product stream is taken off via line (4) and fed to further processing. The desired filling level in the continuously operated reactors is controlled in accordance with the prior art. When a cascade is used, the gas phase can be fed through the continuously running liquid stream either in cross-flow (FIG. 2) or in counter-current flow (FIG. 3). Cross-flow in this case means that the reaction gases are fed in via the lines (12), (13) and (5) (FIG. 2) and are taken off again, together with the reaction water and entrained starting material (II) at the respective upper end of each reactor via the lines (8), (7) and (6) (FIG. 2), i.e. the reaction gas flows through the reactors transversely to the direction of flow of the liquid phase. In the case of separate oxygen addition, this is performed via the lines (9), (14) and (15). The starting material (II) is separated off in the separation means (H), (I) and (J) and returned to the respective reactors. The excess reaction gas leaves the reactor together with the reaction water via the lines (8'), (7') and (6'). The reaction water, after the exhaust gas streams have been combined, is removed from the reaction gas in accordance with the prior art. The reaction gas is then fed back to the reactors (A), (B) and (C) together with the replacement of the reaction gas consumed.

The total amount of the reaction gas added can be distributed among the individual reactors as desired. In each reactor, counter-current flow of liquid phase and gas phase is preferably realized.

Counter-current flow (FIG. 3) means that the gas phase is fed into the last reactor (in FIG. 3, reactor C), is continuously conducted through the lines (6) and (7) against the liquid phase running from the first reactor (A) to the last reactor (C in FIG. 3) and is reintroduced at the respective lower end of the following reactor (B) and (A). In the case of separate oxygen addition, this is performed via the lines (9), (14) and (15). Addition and conduction of the liquid phase in the reactors is identical to the cross-flow technique. At the upper end of the first reactor (A in FIG. 3), the excess reaction gas is taken off via line (8) together with the reaction water and entrained starting material (II). In the separation means (H), the majority of the starting material (II) is separated off and returned to the reactor (A). The excess reaction gas leaves the reactor together with the reaction water via the line (8'). The reaction water is removed from the reaction gas according to the prior art and then fed back to the reactor (C) together with the replacement of the reaction gas consumed.

The liquid reaction mixture can be worked up, e.g., by distillation, the aromatic hydroxyl compound first being separated off and the aromatic carbonate being isolated in a further step. The catalyst components situated in the residue can be recovered and recycled.

The following examples clarify the process according to the invention, but without restricting it thereto.

EXAMPLE 1

In an autoclave (11) having a gas-introduction stirrer, cooler and downstream cold trap, 0.34 g of palladium bromide and 8.31 g of tetrabutylammonium bromide were dissolved in 450 g of phenol at 80° C. To activate the catalyst, carbon monoxide (3 l/h) was passed through this solution for one hour. 0.77 g of manganese(II) acetylacetonate and 2.21 g of sodium phenolate dissolved in 50 g of phenol were then added and the pressure was adjusted to 10 bar with the introduction of a gas mixture of carbon monoxide and oxygen (95:5% by volume). The flow rate of the gas mixture composed of carbon monoxide and oxygen (95:5% by volume) was set to 400 l (S.T.P.)/h. A sample was removed from the reaction mixture every hour and analysed by gas chromatography. The analyses showed that the reaction mixture contained 8.2% diphenyl carbonate after 1 hour, 13.75% diphenyl carbonate after 2 hours and 18.6% diphenyl carbonate after 3 hours. 8.75 g of a phenol/water mixture had condensed in the cold trap.

Catalyst cycles per hour: 113 (average)

Space-time yield: 31 g/l-h (average)

The catalyst cycle in this case denotes mols of diphenyl carbonate formed per mol of Pd compound per unit time.

COMPARISON EXAMPLE 1

The experiment as described in Example 1 was repeated, but instead of 400 l (S.T.P.)/h, only 6 l (S.T.P.)/h of the carbon monoxide/oxygen gas mixture were introduced. The gas chromatographic analysis of the samples showed that the reaction mixture contained 4.8% diphenyl carbonate after one hour. The reaction mixture contained 5.3% diphenyl carbonate after 2 hours and 5.4% diphenyl carbonate after 3 hours. 0.2 g of a phenol/water mixture had condensed in the cold trap.

EXAMPLE 2

In a bubble-column reactor (5 cm in diameter and 50 cm in height) having a cooler and downstream cold trap, 0.34 g of palladium bromide and 8.31 g of tetrabutylammonium bromide were dissolved in 450 g of phenol at 80° C. To activate the catalyst, carbon monoxide (3 l/h) was passed through this solution for one hour. After activation was completed, 0.77 g of manganese(II) acetylacetonate and 2.21 g of sodium phenolate dissolved in 50 g of phenol were added and at 10 bar a gas mixture (600 l (S.T.P.)/h) composed of carbon monoxide and oxygen (95:5% by volume) was introduced. A sample was taken from the reaction mixture every hour and analysed by gas chromatography. The analyses showed that the reaction mixture contained 9.6% diphenyl carbonate after one hour, 17.2% diphenyl carbonate after 2 hours and 23.0% diphenyl carbonate after 3 hours. 11.3 g of a phenol/water mixture had condensed in the cold trap.

Catalysis cycles per hour: 143 (average)

Space-time yield: 38.3 g/l -h (average)

EXAMPLE 3

Example 2 was repeated, but instead of 0.34 g, only 0.08 g of palladium bromide was used and the reaction procedure was carried out at 8 bar and 300 l (S.T.P.) of gas mixture. The palladium bromide excess was decreased in this example. Manganese(II) acetylacetonate was already added before the activation of the palladium.

A sample was taken from the reaction mixture hourly and analysed by gas chromatography. The analyses showed that the reaction mixture contained 12.5% of diphenyl carbonate after one hour, 16.2% diphenyl carbonate after 2 hours and 21.5% diphenyl carbonate after 3 hours. 12.1 g of a phenol/ water mixture had condensed in the cold trap.

Catalyst cycles per hour: ø 486 (average)

Space-time yield: 37.5 g/lb (average)

What is claimed is:

1. A process for the preparation of an organic carbonate of the formula (I)

R—O—CO—O—R (I)

in which

R denotes an unsubstituted or substituted $C_6$–$C_{12}$-aryl, by reacting an aromatic hydroxyl compound of the formula (II),

R—O—H (II), in which

R has the meaning given above, with carbon monoxide and oxygen in the presence of an activated noble metal catalyst which was prepared from a compound of a noble metal of group VIIIb of the Periodic Table of the Elements (Mendeleev) in the presence of a quaternary salt by treatment with carbon monoxide in liquid phase at elevated temperature, a cocatalyst, a quaternary salt and a base, wherein the reaction water is removed from the reaction mixture by excess reaction gas.

2. The process of claim 1, wherein the reaction gas is introduced in an amount of 1 to 100,000 l (S.T.P.) per liter of reaction solution.

3. The process of claim 2, wherein the reaction gas is introduced in an amount of 5 to 50,000 l (S.T.P.) per liter of reaction solution.

4. The process of claim 3, wherein the reaction gas is introduced in an amount of 10 to 10,000 l (S.T.P.) per liter of reaction solution.

5. The process of claim 1, wherein the reaction gas used is a mixture of carbon monoxide, oxygen and an inert gas, and the concentration of the inert gas in the reaction gas being 0–30% by volume.

6. The process of claim 5, wherein the inert gas forms an azeotrope with water.

7. The process of claim 5, wherein the inert gas in the reaction gas is 0–15% by volume.

8. The process of claim 7, wherein the inert gas in the reaction gas is 0–5% by volume.

9. The process of claim 1, wherein the reactors used are stirred tanks or bubble columns, these being able to be used as individual reactors or as a cascade.

10. The process of claim 9, wherein in a reactor cascade 2 to 15 reactors are connected one after the other.

11. The process of claim 10, wherein 2 to 10 reactors are connected one after the other.

12. The process of claim 11, wherein 2 to 5 reactors are connected one after the other.

13. The process of claim 1, wherein the noble metal is palladium.

14. The process of claim 1, wherein the organic hydroxyl compound used is phenol.

15. The process of claim 1, wherein the base used is a tertiary amine, alkali metal phenolate or alkali metal salt of weak acids.

16. The process of claim 15, wherein the base used is an alkali metal carboxylate or an alkali metal phenolate.

17. The process of claim 16, wherein the base used is an alkali metal phenolate.

18. The process of claim 1, wherein the quaternary salt used is a tetraalkylammonium or tetraalkylphosphonium salt.

19. The process of claim 18, wherein the quaternary salt used is a tetraalkylammonium salt.

20. The process of claim 1, which is carried out at 30° to 200° C. at a pressure of 1 to 100 bar and with stirring.

* * * * *